United States Patent
Zachariou et al.

(12)

(10) Patent No.: US 6,214,975 B1
(45) Date of Patent: Apr. 10, 2001

(54) METHOD FOR EVALUATING TARGET PROTEIN QUALITY FROM FERMENTER

(75) Inventors: Michael Zachariou, Walnut Creek; Jonathan Mazer, Winters; Hyun J. Park, Los Angeles; Charles Olson, Moraga, all of CA (US)

(73) Assignee: Bayer Corporation, Berkeley, CA (US)

( * ) Notice: Subject to any disclaimer, the term of this patent is extended or adjusted under 35 U.S.C. 154(b) by 0 days.

(21) Appl. No.: 09/466,711

(22) Filed: Dec. 17, 1999

(51) Int. Cl.$^7$ .............................. C07K 17/00; C07K 1/00; C12P 21/00; A61K 35/14
(52) U.S. Cl. ....................... 530/412; 530/350; 530/383; 435/69.1; 435/69.6; 435/70.1; 435/813; 435/814
(58) Field of Search .................................. 435/69.1, 69.6, 435/70.1, 813, 814; 530/412, 350, 383

(56) References Cited

PUBLICATIONS

Kennel et al. Monoclonal Antibody Rat CD63 Detects Different Molecular Forms in Rat Tissue. Hybridoma 17(6): 509–515, 1998.*

Mao et al. Predicting the Performance of Chromatographic Columns in Protein Purification Processes. Australasian Biotechnology 2(2): 112–116, 1992.*

* cited by examiner

*Primary Examiner*—Christopher S. F. Low
*Assistant Examiner*—Holly Schnizer
(74) *Attorney, Agent, or Firm*—James A. Giblin; Michael J. Beck

(57) ABSTRACT

A chemiluminescence-based gel assay may be used as an indicator of fermenter health. The assay is performed using a sample of fermentation medium essentially directly from the fermenter (with no need for complicated purification of the sample before performing the assay). Results from the assay may be correlated with the final product purification yield of a given protein/purification protocol system. This may then be used as a predictor of purification yield before actually performing the purification.

5 Claims, 1 Drawing Sheet

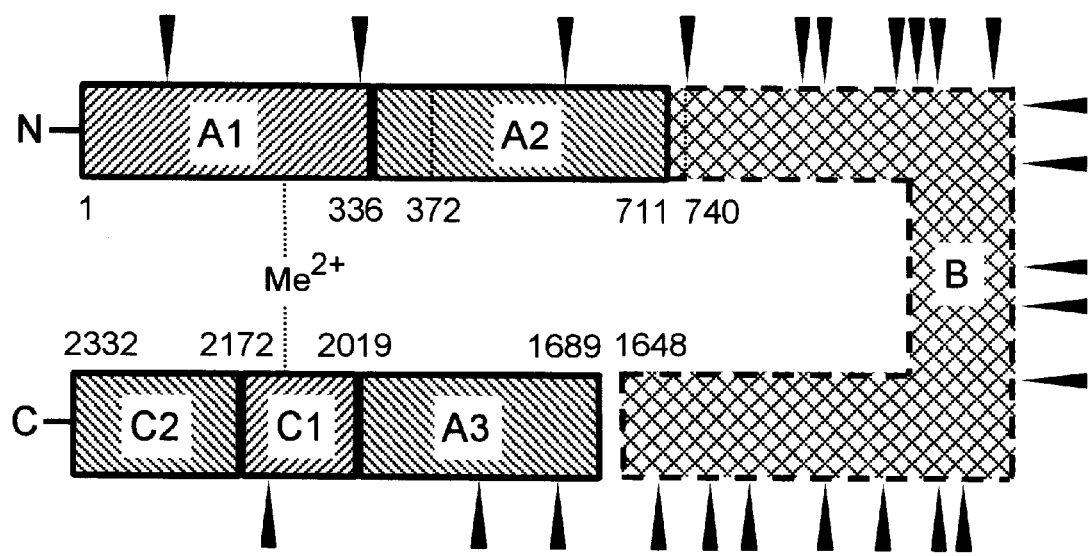
FIG._1
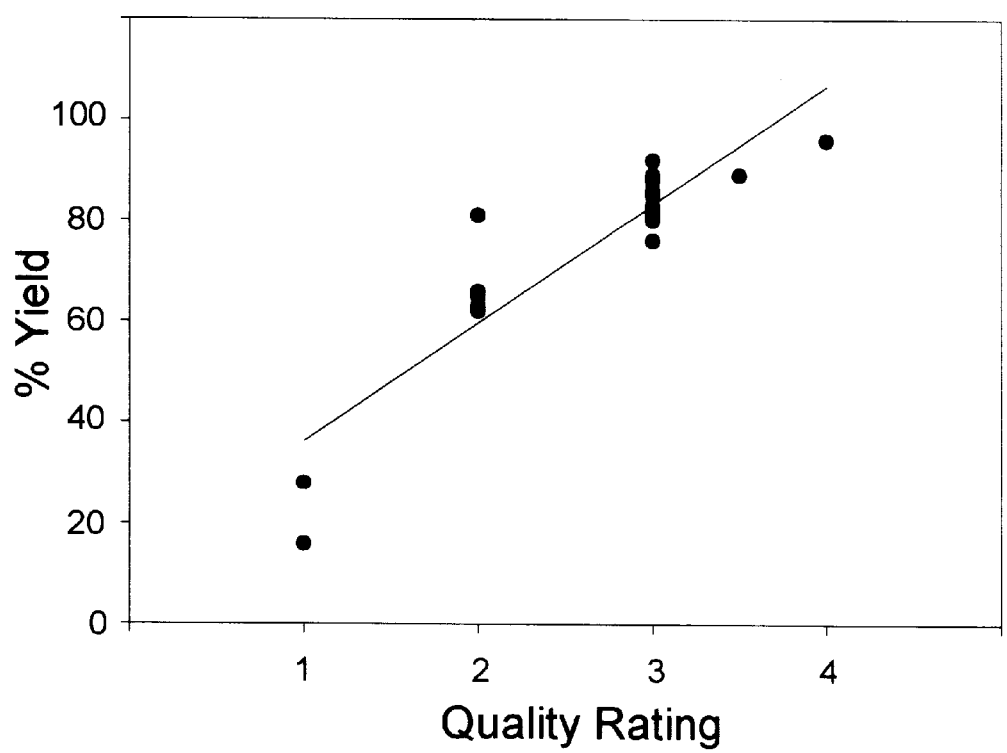
FIG._2

METHOD FOR EVALUATING TARGET PROTEIN QUALITY FROM FERMENTER

BACKGROUND OF THE INVENTION

1. Field

The present invention relates generally to the production of target proteins in cell culture, and specifically relates to a method of assaying a sample of the cell culture medium to evaluate the quality of the target protein in the sample.

2. Background

Blotting procedures have been cited in the literature since 1975 when Southern published his method of DNA fragment identification after transfer of the DNA from a gel to a nitrocellulose membrane (Southern, 1975). This type of macromolecular transfer was followed by the transfer of RNA onto a filter matrix, which was termed Northern blotting (Alwine et al., 1977). The transfer of proteins from gels onto membranes occurred in 1979 and was termed Western blotting (Towbin et al., 1979). Since then, numerous reviews have been written describing protein blotting (Dunbar, 1994; Gershoni, 1988). The immobilization and detection of proteins generally involves five basic steps. The first step is the electrophoresis of the proteins on a PAGE-gel. Next, the proteins are transferred from the gel and immobilized onto a membrane. Third, non-specific sites on the membrane are blocked so as to increase the signal to noise ratio. The fourth step includes the binding of specific antibodies to the immobilized proteins and subsequent binding of a secondary antibody that recognizes the primary antibody. Finally, the secondary antibody is detected via a detection system, typically involving an enzymatic reaction.

The four main detection systems used on immunoblots are radiometry, calorimetric, bioluminescence, and chemiluminescence. Radiometry involves labelling the samples/antibodies with radioisotopes and exposing the blot to autoradiography film. Although this procedure is sensitive it requires the handling and disposal of radioisotopes and a radioactivity safe facility. Furthermore, the exposure time to the X-ray film is much longer than that for other detection methods. Colorimetric detection methods involve using a secondary antibody that is conjugated to an enzyme, for example alkaline phosphatase, which will react with a colored substrate such as bromochloroindolyl phosphate and nitroblue tetrazolium, to produce a color wherever the antigen/primary antibody complex has reacted with the secondary antibody. The colorimetric method is more sensitive and faster than the radioactive method but does not give a permanent hard copy and is not as sensitive as chemiluminescence or bioluminescence.

More recently, detection systems that have focused on the detection of light have become more common because of their high sensitivity and prolonged and rapid signal output. Bioluminescence and chemiluminescence are the two most sensitive detection methods used for Western blotting). Although both involve the emission of light, they primarily differ in the substrate they use. Bioluminescence substrates such as luciferin are natural products while chemiluminescent substrates such as luminol are made synthetically. Bioluminescence detection involves the release of activated luciferin from luciferin-o-β-galactoside by β-galactosidase during its interaction with an alkaline phosphatase conjugated secondary antibody. The luciferin is oxidized to oxyluciferin by luciferase, with light being a product of the reaction. This technique has allowed the detection of as little as 5 fg of protein (Geiger, 1994).

Chemiluminescence involutes the oxidation of a peracid salt by horseradish peroxidase (HRP) that is conjugated to a secondary antibody. This oxidation reaction raises the oxidation state of the HRP heme group. As the electron attempts to come back to its ground state it reacts with lumincil to form a luminol radical. As the luminol radical decays it emits light, which is then detected on an autoradiography film. The use of enhancers can prolong the luminol decay for up to 24 hours, which is the main advantage of chemiluminescence over bioluminescence. Chemiluminescence is as sensitive and rapid (often only a few seconds of film exposure is necessary) as bioluminescence. The sensitivity of the chemiluminescence can be significantly improved if the secondary antibody has been conjugated with biotin. This complex can then be exposed to avidin conjugated HRP conjugate and reacted with the luminol reagents. Chemiluminescence is a preferred method of detection because of its high sensitivity, its rapid speed of detection, its prolonged emission time as well as the ready availability of reagents in a kit format from a large number of suppliers.

Common applications of Western blotting include immunodetection of antigenic sites on polypeptides and for amino acid sequencing. Other applications for Western blots include the detection and characterization of glycoprotein carbohydrate chains (Sato et al., 1998) and detection of receptors zand the study of protein-protein interactions. This has all been made possible by the extensive and sensitive detection methods used in immunoblotting. Most applications, however, have been confined to confirming the presence or absence of product in cell extracts and not for assessing the overall quality of the product for the prediction of downstream purification yields. (Kennel et al., 1998).

SUMMARY OF THE INVENTION

A sensitive, generic, electrophoretic based method has now been developed for assessing the quality and the potential for purification of target proteins directly from fermenter harvests, without any need for concentrating the sample. This has been demonstrated with recombinant Factor VIII (rFVIII) produced by a BHK (baby hamster kidney) cell line.

In a preferred embodiment the technique involves running a desalted sample of growth medium on SDS-PAGE followed by Western blot assay using antibodies which bind the target protein, e.g. anti-Factor VIII monoclonal antibodies. This technique provides a significant improvement in sensitivity over conventional Western blot detection techniques. A similar approach has been used previously to characterize proteolytic fragments of rFVIII during cell culture (Kaufmnan et al., 1988). Routine detection as low as 4 ng of target protein has been accomplished by utilizing chemiluminescent substrates in combination with an amplification system having an anti-mouse biotinylated secondary antibody that reacts with avidin-labelled horse-radish peroxidase. Furthermore, this assay has a high throughput and therefore is particularly useful during fermentation development for rapid screening of multiple fermenter conditions and ultimately for determining the potential for purification. The assay has also been applied to the successful prediction of purification process yield.

We have quite surprisingly found that the chemiluminescent Western blot method (ZAP method) correlates well with other assays which can be more difficult and time consuming to perform. The ZAP method described herein is thus particularly useful as an alternative to those assays (since the only method of monitoring rFVIII in the fermenter is by activity titer). The ZAP method can be correlated with purification yields and can be used to demonstrate that the usual method of monitoring rFVIII (activity titer) is not predictive of product quality. It is not the purpose of this report to assign a cause for any of the examples indicated below but rather to demonstrate that the ZAP method can be a sensitive tool under a variety of conditions. A qualitative classification system was designed and used in conjunction with the ZAP method to categorize the quality of a fermenter and its harvest for monitoring purposes. Furthermore, the ZAP method can be used in conjunction with the qualitative classification system to determine the potential of the harvest for purification processing, without having to actually carry out the purification on each sample.

The purification process can be any optimized series of steps to provide a substantially pure product, i.e., particularly free of cellular contaminants, preferably resulting in a product which is at least 60% pure, preferably at least 80% pure, more preferably at least 90% pure, still more preferably at least 95% pure, or most preferably at least 98% pure. The steps may include standard purification procedures well known in the art (see, generally, Scopes (1987) and Deutscher (1990)), with selection of individual steps depending on what other components are in the sample. Standard purification methods include electrophoretic, molecular, immunological and chromatographic techniques, including ammonium sulfate precipitation, density gradient centrifugation, solvent extraction, gel electrophoresis, ion exchange chromatography, size exclusion chromatography, hydrophobic interaction chromatography, immobilized metal affinity chromatography (IMAC), affinity chromatography, reversed-phase HPLC chromatography, and chromatofocusing. Ultrafiltration and diafiltration techniques, in conjunction with protein concentration, are also useful.

FIG. 1 schematically represents the structure of rFVIII. Recombinant FVIII is a glycoprotein with an approximate molecular weight of 290 kD and includes multiple domains. In the intact rFVIII molecule the A1 domain (at the N-terminus), the A2 domain, and the B domain are all linked as a single polypeptide chain of an accumulated molecular weight of about 210 kD. The 210 kD polypeptide chain is linked via the A1 domain by a metal ion to a smaller polypeptide chain that is about 80 kD. The 80 kD domain contains a C2 domain at the C-terminus, a C1 domain, and an A3 domain. Recombinant FVIII from mammalian cells has been shown to have a high level of structural heterogeneity caused by different levels of glycosylation and intracellular processing. In FIG. 1 the potential glycosylation sites are indicated by the triangles. These different processed products will have varying molecular weights and as such can be separated on an SDS-PAGE gel and subsequently be detected on the Western blot.

A high degree of processing suggests that there may be problems in clearing these products during downstream purification. It may also imply that these species are by-products of extracellular proteolysis that occurred once the target molecule had been secreted into the medium. Another possibility is that the cells are being stressed by a certain fermentation parameter so that they either produce large amounts of extracellular proteases, which clip the target molecule, or that they initiate an unacceptably high degree of internal processing. The damaged product and low productivity fermentations resulting from any of these scenarios is not always detected by the usual activity assays (e.g. coagulation titer of FVIII). The ZAP method provides another analytical tool for assessing the quality of the product and the productivity of a fermentation.

BRIEF DESCRIPTION OF THE FIGURES

FIG. 1 schematically illustrates the structure of factor VIII. Potential glycosylation sites are indicated by triangles. Amino acid position is numbered conventionally, starting with the N-terminus and ending at the C-terminus.

FIG. 2 is a graph showing the correlation of overall yield vs. ZAP quality rating.

SPECIFIC EMBODIMENTS

Materials and Methods

Desalting of Samples:

A detailed list of desalting reagents is given in Table 1. Frozen samples (stored at −70° C.) in either 15 or 50-ml centrifuge tubes were thawed in room temperature water for not more than 10–15 minutes, vortexed, then placed on ice. During the thaw period, an appropriate number of Econo-Pac™ disposable desalting (10 ml) chromatography columns were placed in a PolyColumn™ rack. Each sample was desalted in a separate (labeled) column. The column tops and plugs were removed and the liquid drained into the rack buffer tray. Each column was filled to the top and equilibrated with approximately 20 ml of 1×dialysis buffer. After the column stopped dripping, exactly 3 ml of thawed sample were pipetted into the column and allowed to migrate onto the resin. When the dripping stopped, labeled 15 ml (decapped) centrifuge tubes were placed under each respective column. Exactly 4 ml of 1×dialysis buffer were pipetted into the column and allowed to migrate into the resin. Samples of 4 ml were collected in each tube. After the dripping stopped, the tubes were capped, vortexed, and placed on ice. (Samples were stored at −70° C. for later analysis.)

TABLE 1

Desalting Reagents and Supplies

1) Econo-Pac ™ 10 DG Disposable Desalting (30 × 10 ml) Columns (Bio-Rad, Hercules, CA)
2) PolyColumn ™ Rack (Bio-Rad)
3) FALCON brand BlueMax ™ Disposable polystyrene 15-ml centrifuge tubes with caps (VWR, Bridgeport, NJ)
4) 10X Dialysis Buffer, pH 7.4 (0.5 M TRIS, 1.5 M NaCl, 25 mM CaCl2, 0.1% Tween 20)
5) 1X Dialysis buffer

SDS-PAGE:

A detailed list of SDS-PAGE reagents is given in Table 2. Samples were prepared for SDS-PAGE as soon as possible after desalting. Usually 33 µl of each sample was pipetted into a corresponding (labeled) microcentrifuge tube. To each tube 5 µl of 10× reducing agent and 12 µl of NU-PAGE 4×LDS sample buffer were added to make 50 µl of total sample volume. The samples were vortexed and then heated at 70° C. to 100° C. for 2–10 minutes in a heating block. (Water was added to each block well to insure uniform heating of the tubes.) The well location was marked on one or two pre-cast 4–12% gels with a (Sharpie™) pen and the gels were placed into an Xcell II mini-cell SDS-PAGE box. Approximately 200 ml of 1×MOPS buffer (1×) containing 500 µl anti-oxidant was placed into the top reservoir of the gel box. Samples, molecular weight markers, and rFVIII standard were loaded into wells. When all samples were loaded into lanes, the bottom buffer well was filled approximately ¾ full with 1×X MOPS buffer (without anti-oxidant). The gels were run at 200 volts until the blue dye front reached the bottom and started to migrate out of the bottom opening (approximately 45–60 minutes). While the SDS-PAGE was running, the Western blot apparatus was set up to receive the gels. A plastic tray was filled with approximately 200–300 ml of 1×transfer buffer. For each gel being run on SDS-PAGE, 2 transfer sponges (part o the mini-transblot cell transfer apparatus), 2 mini-transblot filter papers, and 1 nitrocellulose paper were placed in the tray and any air bubbles were removed. When the SDS-PAGE gels were finished running, the gels were removed from the box.

TABLE 2

SDS-PAGE Reagents and Supplies

1) Xcell II Mini-cell SDS-PAGE box
2) NUPAGE ™ 4–12% Bis-TRIS (pre-cast) gels, 1.0 mm with 12 wells
3) NuPAGE ™ MOPS SDS (20X) Running buffer
4) NuPAGE ™ (10X) anti-oxidant
5) NuPAGE ™ (10X) Sample Reducing Agent
6) NuPAGE ™ (4X) LDS Sample Buffer
7) Molecular Weight markers: SeeBlue Pre-Stained Standard and MultiMark Multi-Colored Standard
8) Heating Block, model 2002 with 3 module blocks, model 2069 (Lab-Line)
9) Microcentrifuge tubes-(0.5 ml or 1.7 ml)
10) rFVIII positive control standard; diluted to a final concentration of $0.01 U/\mu l$ using 10X Sample Reducing Agent, and 4X LDS Sample Buffer at the appropriate volumes. This solution is heated to 70° C. for 5 minutes, then stored at –70° C. as 20–25 $\mu l$ aliquots. Each aliquot is used once (i.e. thawed aliquots are not refrozen).

Reagents and supplies 1–7 are purchased from NOVEX (San Diego, CA).

Western Blotting:

A detailed list of Western blot analysis reagents is given in Table 3. Immediately upon removal of the gels from the electrophoresis box, they were placed in the plastic tray containing the 1×transfer buffer and all of the materials listed in the SDS-PAGE procedure. A transfer "sandwich" was created as follows (use gloves): A sponge was first placed at the bottom of a tray so that it was covered with transfer buffer. A filter paper and then the nitrocellulose membrane were placed on top of the sponge. The gel was placed carefully onto the membrane so as to prevent tearing and to recognize its orientation, followed by the second filter paper and the second sponge. This entire "sandwich" was very carefully placed inside the plastic transfer cassette, which was then placed inside the transfer box. The transfer was runt overnight at 25–50 Volts. Typically, 35 volts for 16 hours gave good results. After transfer, the membrane was removed from the sandwich and placed in blocking buffer for 60 minutes at 37° C. with mild shaking on the lab rotator. Hereafter, all antibody incubations and wash steps were at 37° C. with mild shaking on the lab rotator. The membrane was washed in 50–100 ml of 1×TBST, 4 times for 5 minutes each. The primary antibody dilution factors were determined experimentally to compensate for the titer of a specific lot. Typically, the concentrations used were: R8B12 was at 107.5 $\mu g$ in 20 ml (1×) TBST and C7F7 was at 231 $\mu g$ in 20 ml (1×) TBST. The primary antibodies were either used alone or in combinations at the same concentration listed. The membrane was incubated sequentially with primary (1°) antibody (at the appropriate dilution), a 1:100,000 dilution of goat anti-mouse biotinylated secondary (2°) antibody, and a 1:500,000 dilution of HRPase-conjugated NeutrAvidin™. Each incubation lasted for 1 hour and was followed by a washing step. The membrane was incubated in 6–10 ml total volume of a 1:1 mixture of the SuperSignal West Femto Maximum Sensitivity Substrate™ chemiluminescent reagents for 1 minute (at room temp) with mild shaking by hand. Saran wrap was folded over the membrane so as to avoid bubbles between the wrap and the membrane and excess wrap was cut away with a scissors. The membrane was exposed to film in a film cassette for a measured amount of time. Film exposure times were adjusted as needed to clearly detect bands; typically, between 1 and 30 seconds was sufficient.

TABLE 3

Western Blot Reagents and Supplies

1) Mini-TransBlot Cell transfer box apparatus (Bio-Rad)
2) NuPAGE (20X) Transfer buffer (NOVEX) (2 Liters of 1X Transfer buffer is made as follows: 100 ml 20X Transfer buffer, 200 ml A.C.S. methanol, 2 ml 10X anti-oxidant, 1698 ml water)
3) Nitrocellulose paper, 0.2 $\mu m$ (8 × 8 cm) (Pierce, Rockford, IL, USA)
4) Mini-TransBlot Filter Paper (Bio-Rad)
5) High Current Power Supply, model VWR570 (VWR)
6) Stir plate (VWR)
7) Plastic (324L × 260W × 70H mm) tray (VWR)
8) ISS or Tupperware trays
9) Low Temperature/B.O.D. Incubator, model 2005 (VWR)
10) Lab-Line brand (platform) Lab Rotator, model 1314 (VWR)
11) Superblock Blocking Buffer in PBS (Pierce)
12) TRIS-buffered Saline with Tween 20, or "TBST" (Made as a 4X concentrated stock solution: 80 mM TRIS-base (pH 7.4), 2 M NaCl, 0.2% Tween 20)
13) Goat Anti-mouse ImmunoPure ™ Biotinylated Secondary Antibody (Pierce) (Diluted to 1:100,000 final dilution).
14) NeutrAvidin ™ Horseradish peroxidase-conjugated (HRP) (Pierce) (Diluted to 1:500,000 final dilution).
15) SuperSignal BLAZE ™ Chemiluminescent Substrate (Pierce)

TABLE 3-continued

Western Blot Reagents and Supplies

16) Saran wrap (VWR)
17) Hyperfilm ECL High Performance Chemiluminescent Film (Amersham Pharmacia Buckinghamshire UK)
18.) Medical Film Processor, model QX-70 (Konica)
19.) Film Exposure (8 x 10 in.) Cassette (Sigma, St. Louis, MO) with 2 DuPont Cronex ™ "Lightening Plus" enhancer screens This procedure is designed as an ultra-sensitive analytical method for the detection of femtomolar amounts of a protein. The following non-limiting examples demonstrate optimized analysis of rFVIII from BHK cell fermenters and harvests.

EXAMPLE 1

Optimization of the Method in rFVIII Production:

The ZAP method was optimized for determination of the presence of the 210 kD, the 80 kD and any other truncated or unprocessed forms of rFVIII which exhibit rFVIII-type antigenicity to the antibodies. The 210 kD and 80 kD in appropriate ratios served as indicators of intact rFVIII (and hence good fermenter health) while any other fragments served as indicators of different degrees of product fragmentation (and hence poor fermenter health). The combined indicators were incorporated into a classification system that was used to determine the quality of the product, the potential for providing high yields from the purification train, as well as the general health state of the fermenter (see Table 5 for classification system).

Many aspects of the ZAP technique were investigated for optimization purposes. These elements were studied in se-quence beginning with the optimization of the sample preparation and including the desalting step, the type of SDS-PAGE gel, the type of blotting paper, the type of blocking buffer, optimizing primary and secondary antibody concentrations, optimizing the avidin concentrations, evaluating vendor chemiluminescent reagents. Although this technique has many variables, not all were optimized since the variables that were optimized resulted in a method that provided satisfactory results.

Sample Preparation:

Initially, carrying out an acetone precipitation after the desalting of the sample was necessary to see strong bands on the ZAP since the ZAP methodology had not been optimized for sensitivity. Once the ZAP sensitivity was optimized the necessity of the acetone precipitation step was re-evaluated. Eliminating the acetone precipitation step from the ZAP methodology was viewed as critical since it would accelerate the process by 3 to 4 hours and also improve the reproducibility of the technique.

One problem with carrying out acetone precipitation is that all traces of acetone need to be removed prior to SDS-PAGE. In some cases, especially when there is a large sample number, there may be a sample in which the acetone has not been fully evaporated. Failing to evaporate a significant portion of the acetone was observed to result in smearing of the sample on the gel. In this case, it was impossible to obtain any information about the sample.

Carrying out the ZAP without having to do an acetone precipitation improved accuracy, reproducibility, and quality of the results as well as significantly reducing the time for the process.

Desalting:

It was found that including 0.01% Tween 20 into the sample prior to desalting led to signal enhancement, apparently by preventing non-specific interactions with the desalting column. In practice, the range of Tween (or any other non-ionic surfactant) may need to be adjusted to yield optimum results, for example between about 0.001% and about 1.0%, or more preferably between about 0 01% and about 0.2%.

Selection of SDS-PAGE Gels:

SDS-PAGE gels were examined from two different vendors to observe their impact primarily on protein transfer. Gels from Novex and FMC (Roskland, Me.) were compared. The gels from both vendors were developed by chemiluminescence as described in the materials and methods section. The Novex gel had a lower background than the FMC despite both gels being run and developed under identical conditions. It was also noted that the FMC gel was more difficult to manipulate during transfer and was very brittle. As a result, the FMC gel fell apart during our handling. We concluded that Novex gels would be preferred, though other gel products commercially available could potentially be used in the assay, also.

Blotting Paper:

Nitrocellulose and polyvinyldivinyl fluoride (PVDF) membranes were compared for carrying out transfers from SDS-PAGE gels. A significant improvement of signal to background ratio was observed when using nitrocellulose. Such a result is to be expected since, because of their hydrophobic nature, PVDF membranes tend to bind more proteins than nitrocellulose, which is a relatively more inert membrane.

Blocking Buffer Formulation:

Blocking buffers were used to quench any non-specific binding onto the membrane thereby reducing background staining. Some of the common blocking reagents include bovine serum albumin, gelatin, Tween 20 and a variety of non-fat milk products. We tested bovine serum albumin, non-fat dry milk (from a variety of sources), as well as a commercially available blocking agent of unspecified constituency from Pierce, known as SuperBlock™. Tween 20 (0.05% v/v) was in all blocking solutions tested except for SuperBlock which was tested at 0.01%, 0.05% and 0.2% v/v Tween 20 solutions.

The blocking buffer solutions were evaluated based on their ability to provide a low background as judged by the absence of the molecular weight markers and a lightening of the background. The inability to quench the signal from the molecular weight markers was an indication that the blocking buffers still allowed some cross-reactivity to occur between the primary antibodies and the molecular weight markers. This would indicate that the buffers may then also not be sufficiently blocking BHK cell antigens from the fermenter that the primary antibodies may cross-react with. The 10% non-fat dry milk from BioRad was found to be superior to the other blocking buffers tested since it produced very low background and was able to quench all of the molecular weight markers. As a result, we chose 10% non-fat dry milk from BioRad as our preferred blocking buffer.

It must be noted that this is only the blocking buffer of choice for this specific system. It may be necessary to five, six, or more different antibodies being selected in preferred embodiments.

TABLE 4

Attributes of antibodies tested

| Monoclonal Antibody | Attribute | Result |
| --- | --- | --- |
| 19A9 | Directed against the B-domain | Positive but too many bands-Not chosen |
| 58.12 | Directed against 90kD portion of 210kD fragment | Negative, too faint-Not chosen |
| C7F7 | Directed against N-terminus of the 80kD | Positive, 80kD clearly observed; not antigenic to BHK proteins-Chosen |
| R8B12 | Directed against 90kD portion of 210kD fragment | Positive, 210kD clearly observed; not antigenic to BHK proteins- Chosen |
| ESH-4 | Directed against 80kD | Negative; No bands observed. Not chosen |
| ESH-5 | Directed against 80kD | Negative; No bands observed. Not chosen |
| ESH-8 | Directed against 80kD | Negative; No bands observed. Not chosen | optimize the blocking buffer for the particular protein being investigated; the optimization may be accomplished by methods well known in the art and while generally following the examples contained herein, varying process parameters to optimize the desired outcome. As a cautionary note, blocking buffers containing milk products should be investigated carefully if lectins or antibodies that recognize carbohydrate moieties are to be used in the assay, since milk contains large amounts of sugar that may block binding. If this is the case, then we would recommend the use of the SuperBlock buffer with 0.2% Tween.

Selecting Primary Antibodies:

A number of monoclonal antibodies were examined for use on ZAPs as primary antibodies. These were 19A9 (against the B-domain), 58.12 (against the 90 kD N-terminus), C7F7 (against the N-terminus of the light chain), R8B 12 (against the 90 kD) ESH-4 (light chain), ESH-5(light chain), and ESH-8 (light chain). A polyclonal was also tried without much success and is not represented here. Furthermore, the use of a polyclonal would not be as informative as using a monoclonal antibody due to its intrinsic loss of specificity and so was not further pursued. Results are described in Table 4.

Based on the above results, we selected the R8B12 and the C7F7 antibodies as the main primary monoclonal antibodies to be used during Western blot development. Other antibodies such as the ESH antibodies could be used but were not chosen since significantly larger concentrations of these antibodies would need to be used to obtain the equivalent signal as the C7F7 and R8B12 which are available in-house. These antibodies provide us with sufficient information pertaining to the presence or absence of 210 and 80 kD as well as a sufficient number of fragments to inform us of the fermentation quality. We do not need to see every fragment that is; produced in the fermentation since the ones that can be detected by the C7F7 and R8B12, can act as good indicators. Furthermore, too many bands on the ZAP will detract from being able to accurately quantitate the more important 210 kD and 80 kD bands. Other monoclonal antibodies which bind with specificity to rFVIII may be used to yield comparable results, particularly if the antibodies are selected to yield complementary information on the species in the sample. Preferably, more than one antibody is selected, such as two or three different antibodies, with four, The approach one could use to select the primary antibodies for other target molecules is essentially similar to above. The approach can be broken down to two components: Firstly, an understanding of the target molecule's SDS-PAGE profile needs to be known. For example, is the molecule monomeric or multimeric under the chosen SDS-PAGE conditions or are there degradation products or aggregates? Also, determining if the target molecule has isoforms which serve as antigenic sites is critical in choosing the primary antibody. Detection of isoforms can be carried out easily on a 2D-gel with subsequent Western blotting. After the antibodies are chosen on the basis of their target molecule antigenicity, the second step in the process is to ensure that the successful antibodies provide a high "signal to background" ratio. This is done by carrying out a titration of the antibodies in a preoptimized blocking buffer. Along with background reduction, non-specific interaction with the host cell proteins should also be demonstrated. Using such a procedure we have been able to use the ZAP for determining the quality of IL-2.

Selecting Chemiluminescent Reagents:

Chemiluminescent kits were examined for improving the signal to noise ratio. The various kits tested were ECL (Arrersham, Piscataway N.J.), Renaissance (NEN, Boston, Mass.) and BLAZE (Pierce, Rockford, Ill.). All kits were tested as per manufacturer's protocol. The BLAZE reagent was by far the most sensitive and also provided the lowest level of background. The manufacturer claims that it can detect down to femtomole levels of a single protein, and we could routinely detect $7.3 \times 10^{-15}$ moles of rFVIII per well. Other chemiluminescence kits could be used but would need to be optimized for time of exposure and concentration of samples.

The secondary biotinylated antibody supplied with the Pierce kit was titrated over the range of 10,000 to 100,000 against the avidin tagged horseradish peroxidase antibody from 100,000 and 500,000 dilution. The ratio of 100,000 dilution of the secondary to 500,000 dilution of the NeutrAvidin™ worked best.

Qualitative Classification System for Determining Quality Rating:

Samples loaded on an SDS-PAGE gel were usually denatured by the addition of an excess amount of SDS and a reducing agent and then heating at 70° C. to 100° C. for 2 to 5 minutes. Under denaturing conditions the metal ion holding the two rFVIII polypeptides together is dissociated leaving free 210 kD polypeptides and free 80 kD polypeptides. The 80 kD was observed to run as a doublet under normal SDS-PAGE running conditions. These were the main species observed, and if this was the case the quality rating of the product was considered excellent. Other species that were observed included a 90 kD (the A1 and A2 polypeptides processed from the B-domain) and any other combination of molecular weight due to protein processing. Free 80 kD was also observed. The intensity ratio between the 210 kD and 80 kD can serve as an indicator of free 80 kD (e.g. if the 80 kD is more intense than the 210 kD) and as such plays a role in the established qualitative classification scheme outline below. Based on this information, the following qualitative classification system for determining quality rating was established for fermenters and their harvest.

TABLE 5

Qualitative ZAP Classification System (rFVIII)

| Quality Rating (number) | Description |
| --- | --- |
| Excellent or 4 | Strong 210 kD and 80 kD. No fragments under 80 kD or between 210 kD and 80 kD. No bands or smearing above 210 kD. Proceed with purification. |
| Good or 3 | It has a strong 210 kD band and 80 kD band. Has fragments either above the 210 kD or below the 80 kD or between the 210 kD and 80 kD, but not in all areas. May have some low level smearing around and above the 210 kD. Proceed with purification. |
| Fair or 2 | Has a weakening 210 kD and/or 80 kD such that the ratios are different to the standard. Has fragments in more than one zone (ie. <80 kD,> 210 kD or 210 kD to 80kD and has much smearing. If purified will give rFVIII but perhaps lower yield or lower purity may result. |
| Bad or 1 | Missing either the 210 kD, 80 kD or both. Should not be purified. |

Guidelines for a classification system for determining quality rating for a general target protein are given in Table 6.

TABLE 6

Qualitative ZAP Classification System (general target)

| Quality Rating (number) | Description |
| --- | --- |
| Excellent or 4 | Target molecule in its monomeric form is present with no detection of any other antigenic pieces of the target molecule. Target molecule accounts for nearly 100% of the bands seen on the ZAP |
| Good or 3 | Target molecule in its monomeric form represents majority of the bands seen on the ZAP i.e. in excess of 50% but less than 100% |
| Fair or 2 | Target molecule in its monomeric form represents equal or less than the majority of the bands seen on the ZAP i.e. ≦50% |
| Bad or 1 | Target molecule in its monomeric form is either not detectable or not indicative of an intact molecule (e.g., if target is a multimer, such as rFVIII, in the instance one of the target molecule's subunits is missing.) |

EXAMPLE 2
Analyzing Fermenter Growth Conditions:
To demonstrate the general utility of the ZAP assay, the technique was applied to samples from rFVIII producing cells grown under different conditions. Fermentation was conducted either in the presence or absence of human plasma protein solution (HPPS). HPPS consists primarily of albumin but also contains up to 30 other proteinaceous components such as haptoglobin, transtherytin, ceruloplasmin and vitamin D binding protein. HPPS was included in the fermentation medium at 2.25 g/L to help protect rFVIII from instability issues such as proteolysis. Assuming a specific rFVIII activity of 5000 U/mg, an average titer of 1.0 U/ml and that no proteins other than HPPS and rFVIII are present, then rFVIII would represent approximately only 0.009% of the total protein content in these fermentations. This percentage is most likely to be even less if we consider the protein contribution made by BHK cell secretion. Such a poor rFVIII specific activity made it impossible to visualize rFVIII from a fermenter on an SDS-PAGE gel using any type of staining technique. Low concentrations of rFVIII also made it difficult to detect rFVIII from a fermenter using Western blotting with a chromophoric or radioisotope detection system.

The cell fermentation medium used in the fermentation runs conducted in the absence of HPPS had essentially into added protein other than recombinantly-derived insulin (10 mg/L). Insulin is ~5 kD and should not interfere with the primary antibodies. In fact, it may even run off the 4–12% SDS-PAGE gels. The only other proteins, aside from rFVIII, that may have been detected were those secreted by the BHK cells. In fact, an $A_{280nm}/A_{260nm}$ reading of fermenters routinely gave about 0.02 to 0.05 mg/ml level of protein, assuming an extinction ci)efficient of $1.0$ mg/ml.cm$^{-1}$ for 1.0 absorbance unit and corrected for the presence of DNA. The rFVIII titers were routinely about 1.0 U/ml, and so rFVIII represented about 0.4% of the total protein content of harvests from the HPPS-free fermentations. Nevertheless. rFVIII from HPPS-free fermentation was not discernible from any impurities on an SDS-PAGE system with any type of staining technique when the samples are taken directly from the fermenter or harvest lines. Chromophoric detection systems struggled to detect the 210 kD and 80 kD and certainly failed to pick up minor fragments of rFVIII. Chemiluminescence detection was therefore applied to analyze rFVIII from HPPS-free fermentation taken from the fermenter and harvest lines.

Fermenter harvests from both HPPS-containing and HPPS-free fermentations were examined on a Western blot using the chemiluminescence detection method. By using the optimized chemiluminescent method the signal from the 210 kD fragment of rFVIII from the HPPS-containing fermentation matches up Oust as for HPPS-free rFVIII, below) with purified standard rFVIII and is clearly observable. The 80 kD piece is masked by an HPPS component speculated to be transferrin and so cannot be seen. Nevertheless, any degradation that may be induced between the 210 kD and the 80 kD will be seen. The large amount of albumin in the sample is detected non-specifically by the primary antibodies but does not appear to interfere with the clear visualization of the 210 kD band. It may, however, mask rFVIII fragments that have a similar size as the albumin The samples tested showed excellent quality product and would be classified as class 4 type fermenters.

Several samples from HPPS-free fermentations taken from the fermenter and harvest line were also tested. They all represented approximately 0.8 to 1.2 U/ml of rFVIII or 0.08 to 0.012 U/well. The 210 kD and the 80 kD bands seen in the samples ran parallel to the bands from the HPPS-containing sample. This observation, along with the strong reactivity these bands had against the C7F7 and R8B12 monoclonal antibodies, was used as confirmation that the 210 kD and 80 kD bands in the samples were in fact the rFVIII bands. The minor fragments observed in the samples, but not in the rFVIII, were further confirmed to be pieces of rFVIII by probing rFVIII-free BHK (blank transfected) cell harvest with C7F7 and R8B12 and not observing any detectable bands. This experiment served as a negative control and did not reveal any fragments. This observation further supported that the fragments reacting with the C7F7 and R8B12 antibodies were truly pieces of rFVIII and not proteins released by the BHK cells.

EXAMPLE 3
Coagulation Titer vs. ZAPs:

The experiments described in this example were designed to demonstrate that coagulation titer is not always a good predictor of product quality. A physical analysis of the products by ZAP should be used in combination with coagulation titer for determining the properties of rFVIII produced by the fermenter.

In this experiment, rFVIII samples from one particular fermentation run were taken from the fermenter and harvest line and were analyzed by ZAP. The samples had a titer of about 0.87 U/ml, which is considered to be within the acceptable activity range and would normally be processed for purification. The ZAP, however, clearly indicated that although there is an acceptable titer, there is no 210 kD fragment and only some 80 kD. Purification of harvest from this fermenter using the automated purification train, followed by analysis on an SDS-PAGE gel, also indicated the absence of the 210 kD fragment and an overall recovery of only 26%.

These results clearly indicated that this fermentation run was providing an unacceptable product. This is despite all other fermentation parameters, including titer, being normal. Hence, without the ZAP, this fermenter would have been considered to be operating normally and be recommended for proceeding to purification. The outcome would have been a poor yield and, a failed lot.

In the past, coagulation titers have been the main determinant of fermenter-produced rFVIII quality. High coagulation titers were interpreted as a good result while low titers were interpreted as pocor. However, other species in solution may demonstrate rFVIII activity, e.g. fragments of rFVIII or possibly aggregates. The B-domain is not required for coagulation activity since during this particular assay, thrombin is used to cleave the B-domain and obtain active rFVIII (Factor VIIIa) (Pemberton et al., 1997). The A1 and A2 domains only need to be held by electrostatic interactions, and as long as they are metal-bridged to the C2·C1·A3 polypeptide, then there will also be activity. It is also feasible that some truncation of the A1 N-terminus and/or truncation of the A2 and/or A3 C-terminus may still elicit activity. The net result may be disastrous since it may then be interpreted that the fermenter is producing good quality rFVIII, but by the end of the purification process very little activity is recovered. This may be due to the smaller activity producing fragments being purified away because of their differential chromatographic retention. Such truncated forms would, however, translate into a variety of molecular weights on SDS-PAGE and hence be easily detected by the ZAP. By carrying out the ZAP we will be able to verify the extent to which the full molecule rFVIII contributes to coagulation titer in a sample.

EXAMPLE 4
Correlation Between ZAP Classification and Purification Yield from HPPS-free Fermenters:

Until now, it has been difficult to ascertain with any accuracy the recovery of rFVIII from a purification process without carrying out some rapid scaled-down purification process (such as the one described below). In particular, the use of Western blots to predict purification yields (and therefore purification process performance) from an unprocessed fermenter sample has not previously been described in the literature.

The complex nature of the purification process takes purification yield prediction, directly from an unprocessed fermentation sample, difficult. Purification yield is dependent on many parameters including, but not limited to, the level and nature of the protein impurities, the level and integrity of the target molecule and the ratio of these values (i.e., the specific activity of the target molecule). Other parameters include the number of purification steps and the robustness of the process. So many complex variables makes an a priori prediction of the purification yield difficult from a crude fermenter sample. As such, a priori prediction of purification yields using Western blots is novel.

Reducing or even eliminating any extraneously added proteins, such as HPPS, from the fermentation reduces their impact on the purification yield of the target protein. Furthermore, the number of purification steps (where losses of the target protein may occur) necessary to yield a purified product is reduced. This in turn should improve the robustness of the purification process. Hence, by eliminating the extraneous proteins we significantly improve the chances of successfully using an unprocessed fermentation sample to predict purification yield. This is certainly one of the rationales for conducting the fermentation under HPPS-free conditions. The advantages of being able to predict the purification yield from an unprocessed fermentation sample are significant. For example, a manufacturing run can be cut short, before any purification has been carried out on a lot where the purification yield has been predicted to be uneconomical. With such an advantage in mind, an attempt was made to correlate the ZAP classification (as described above) with the rFVIII purification yield obtained from fermenters under HPPS-free conditions.

The small-scale purification train consists of two sequential chromatography steps. The first step uses ANX media, which is a highly crosslinked agarose and is an anion exchange adsorbent from Amersham Pharmacia (Piscataway, N.J.) and primarily binds rFVIII through the B-domain. Binding to the B-domain is most likely through the negatively charged sialic acid groups. The second step is an immunoaffinity step which utilizes an immobilized monoclonal antibody that binds to the light chain. As such, it will bind any whole or fragmented piece of rFVIII that contains the N-terminus of the rFVIII light chain. Being an affinity chromatography step it successfully removes the majority of impurities in addition to any rFVIII that does riot have the light chain attached. After these two columns, the rFVIII (derived from HPPS-free fermentation) is usually at least 80% pure. While ANX media and the immunoaffinity media are preferred materials used in this purification protocal, other similar media are well known to those skilled in the art and may be used with essentially equivalent results, Where the protein of interest is not rFVIII, a separate purification protocol will have to be designed and optimized to suit the protein of interest. Such design and optimization is generally within the capability of those skilled in the art of protein purification.

The purification yield data was obtained from the scaled-down version of the two column anion exchange/immunoaffinity (ANX/C7F7) small-scale purification trains. Percentage yield was calculated by dividing the total number of coagulation units loaded onto the ANX column by the total number of coagulation units recovered from the C7F7 column, and then multiplying by 100%. The same fermenters were analyzed on ZAPs (one day earlier) and classified using the sample classification system described in Table 5. A correlation graph was then draw between ZAP classification and purification yield.

To establish a correlation, as used herein, is to establish a statistical relationship between two sets of data (e.g. the assigned quality ratings and the corresponding yields) by fitting the data to a linear or curvilinear function and obtaining a best fit of the data to the function. The graph in FIG. 2 indicates a correlation coefficient of 0.81 with sample number n=21, if we assume a y=mx+c function. A better fit might be attained if the best fit line is drawn such that it tapers off at the class 1 level and shows more of a saturation effect at class 4. Nevertheless, from class 3 and 4 to class 1, it is observed that the higher the classification level the greater the purification yield. This chart supports the concept that a correlation does exist between purification yield and sample classification such that an approximate prediction of purification yield may be made that is based on ZAPs.

The anion exchange step and the antibody affinity step achieve the majority of the purification and incur the majority of the yield losses. Any additional columns that may be added downstream to the purification process will be primarily for removal of specific impurities such as DNA and/or viruses and it is not anticipated that there will be more than 10 to 15% loss in these steps. This percentage is well within the current error of the correlation graph when using the qualitative classification system and so the impact on the correlation would be minimal. It is not intended that this correlation chart be used where the protein of interest is other than rFVIII. A new correlation profile would need to be established for the protein and its purification protocol. This will easily be accomplished by following the process described herein of classifying ZAP results and correlating them with the purification yields.

Despite the use of a qualitative classification for the ZAPs the correlation between ZAPs and purification yield has been reasonable. The ZAP should now not only be considered as a tool to detect the general health of the fermenter, but also as a predictor of the approximate, overall purification recovery for rFVIII. In fact, such an approach would be amenable for any target molecule, especially where the number of purification steps is small (preferably no more than 3) and the cells are grown in a protein free fermentation medium.

EXAMPLE 5

Using the ZAP to Determine the Quality of IL-2 in Fermenters:

Interleukin-2 (IL-2) is a cytokine with molecular size of approximately 17 kD. It is expressed by a recombinant Chinese Hamster Ovary (CHO) cell line which contains an expression vector coding for the IL-2 protein and which is grown in serum free culture fluid in the fermenter.

Analysis of purified IL-2 on a 2D gel electrophoresis system indicated the presence of up to 17 different isoforms and the presence of dimers as well as higher molecular weight multimers. The selection of antibodies was carried out as described earlier. The antibodies chosen were able to detect all IL-2 isoforms as well as the aggregated forms of the IL-2. Observations are shown in Table 7.

TABLE 7

ATTRIBUTES OF ANTIBODIES TESTED

| Antibody | Attribute | Result |
| --- | --- | --- |
| 20-IR05 | Directed against IL-2; rabbit polyclonal | Positive but too many bands; not antigenic to CHO proteins-Not chosen |
| 10-172 | Directed against IL-2; mouse monoclonal | Positive, all bands seen; not antigenic to CHO proteins-Chosen |
| AF-202-NA | Directed Against IL-2; mouse monoclonal | Signal too weak- not chosen |

Monoclonal antibodies were obtained from Fitzgerald Industries International Inc. #10-172.

Aggregates constitituted very low levels of the IL-2 produced by the fermenters. However, they did represent a loss of IL-2 productivity in the fermenter and so it was desirable to prevent them from forming and preserving them in the monomeric forms. Hence a sensitive Western blot was needed to be used to monitor the aggregates. By using the ZAP for IL-2 detection in the fermenters the relative degree of aggregation was able to be determined.

CONCLUSION

A generic chemiluminescence based assay system (denoted ZAP) to detect antigens on Western blots has been optimized, and its application as a predictor of protein recovery has been demonstrated. The ZAP can be used to characterize the quality of dilute target molecules directly from cell cultures without the need for any purification, in a high throughput manner. Such a technique is ideally suitable for a manufacturing environment where the ZAP can be used to prevent the processing of poor quality product as well as provide data that supports the processing of product where it has been previously unclear if processing should proceed. In both cases, employment of the ZAP would result in improvements in the cost of goods as well as improvement in general efficiency. The ZAP is also ideally suited for use during development of cell lines, fermentation development, and purification process development.

This report describes the optimization of the ZAP to primarily suit rFVIII, but with some minor adjustments it may be applied to any protein, including bikunin, IL-4 and pigment epithelium derived factor, and antibodies such as anti-IL-5. The protein may be obtained from either a procaryotic or a eucaryotic cell growth medium. This is dependent on the availability of antibodies that recognize relevant epitopes of the target molecule. Although not all parameters were examined during the ZAP optimization, the current ZAP protocol is in a functionally optimized format.

The ZAP assay could also be performed using primary antibodies that have been biotinylated. This would decrease the time the assay takes by about 1.5 hours since the HRP conjugated-avidin could be used directly in place of the current secondary antibody. This may also result in an improvement in the signal to noise ratio through the elimination of one of the steps. The use of other antibodies, like 59.7 and 39MH8, which bind to rFVIII may reduce or eliminate the smearing that is associated with the C7F7 primary antibody. Removing the smearing becomes particularly important to enable the ZAPs to be quantitative.

For rFVIII, titer (as measured by the coagulation or chromogenic assay) has been the main method of assessing product quality during fermentations. The optimized ZAP method adds to the existing arsenal of probes that are used to monitor protein production in fermenters by overcoming some of the weaknesses of the existing probes. For example, the ZAP method was used to demonstrate that in some cases, measurable titer might be obtained with truncated forms of rFVIII that are pharmacokinetically unacceptable. Previously, without processing the batch through the purification scheme, it would be impossible to determine the existence of these truncated forms of rFVIII. As a result, either scaled-down purification trains had to be run as indicators of yield or only activity assays were used, and the impact was sometimes reflected by poor yields during purification. By then, however, it would be too late, with much money and time spent arriving at an unsatisfactory conclusion. Using the ZAP method, these truncated forms can be visualized prior to initiating any type of purification process thus improving the efficiency within manufacturing.

The second indicator of product quality has been the yields of the rFVIII after purification. A fully automated, two column, scaled-down version of the initial steps in the purification process was developed as an analytical technique. Although this technique gives an excellent indication of the product yield and purity resulting from the purification process, it has a poor throughput taking 20 hours per sample with a maximum of 4 samples per week, per technician. Alternatively, the gel-based chemiluminescence assay can be run in 8 hours with a throughput of up to 100 samples per week, per technician. It provides a visual characterization of rFVIII quality that can be independent of activity. As such, it can be used to determine if any fermentation should proceed to the purification stage. It can also give a general indication of fermenter health by observing the extent of product fragmentation, which may be a result of aberrant cell metabolism or extracellular proteolysis.

Furthermore, the scaled-down purification does not give any indication of general fermenter health other than rFVIII recovery. Indeed, a Western blot and an SDS-PAGE gel still need to be run to obtain information about purity and product quality. The scaled-down purification version does not give an indication of truncated forms of rFVIII that are produced because of some fermeriter variation that may not ultimately affect purification. This, of course, is irrelevant if we are only studying the effect of the fermentation variable on purification. In some cases, however, such as in the development of a cell line, purification is not always the end goal. The ZAP method is particularly useful in these instances, since it will differentiate truncated forms of rFVIII/proteins that may not have an impact on the purification (i.e. they flow through the columns or bind so tightly that they only come off during the regeneration of the column).

Nevertheless, the ZAP used in conjunction with the quality rating classification system (despite its qualitative rather than quantitative nature) has shown excellent correlation with purification yield. This raises the question of whether small scale purification trains need to be used at all as a tool for revealing product quality or even yield unless further analysis is required, such as a carbohydrate map. The data presented in this report clearly support that ZAPs could replace the need for purification to evaluate product quality. The ZAPs cannot be used during development phases as an a priori tool for predicting purification yield. In this scenario, the ZAP would first require data input from the purification trains in order to establish the classification criteria and to correlate with meaningful recovery yields.

The ZAP method may be extended to allow quantitative evaluation of the antigenic bands. ZAP quantitation would improve the accuracy of purification yield prediction by replacing the qualitative classification system for quality rating currently used with a numerically quantitative range. Furthermore, it would allow for a new correlation to be evaluated between Western blot purity of the fermenter sample and final SDS-PAGE silver stain purity of rFVIII, after purification. This would allow quantitatively reliable purity predictions from ZAPs without carrying out any purification. This is feasible since, at least for rFVIII from HPPS-free fermentation, the final product will be greater than 80% pure, or more typically greater than about 90% or 95% pure, with the remaining species most likely to be truncated forms of rFVIII which have co-purified.

Another contribution that quantitation may allow is the ability to determine the specific activity of rFVIII, not relative to other (non-rFVIII) impurities, but rather to the level of active rFVIII, as well as to the degree of rFVIII heterogeneity. Aspects of this have already been noted in Example 3 where rFVIII standard and fermenter samples which had equal titer showed differences in band intensity. By using an acceptable standard with an accurately known titer, a comparison of the relative intensities to the test samples may be made for determination of the specific activity of rFVIII directly from the fermenter. Determining the specific activity in this way will enable such things as the estimation of contribution that rFVIII heterogeneity has on purification losses, particularly during purification development.

Typically, quantitation is carried out by conventional densitometers that scan the autoradiogram. Although this technique has been used successfully for many years, it is dependent on the optimum performance of the X-ray developing machine and developing solutions. More recently, an Image Station™ from Eastman Kodak (Rochester, N.Y.) has been introduced which is able to directly capture the light output from the chemiluminescing Western blot without the need for exposure onto an autoradiogram. With equivalent sensitivity, the Image Station bypasses the developing machine and eliminates the need for autoradiography. The Image Station is then capable of being used in a densitometry mode where it can quantitate the light emitting bands on the Western blot.

Other potential applications of the ZAP includes its use in the characterization of the glycosylated component of rFVIII. In this case, a lectin could be used to specifically identify the presence or absence of sialic acid groups, directly from the fermenter and without any purification. This would be beneficial in detecting fermenter batches of rFVIII that may have been affected by sialidases.

The ZAP can be a sensitive tool under a variety of conditions. The systematic optimization and development of key steps involved in the Western blot procedure as well as the optimization of the reagents used in the chemiluminescent detection system have been described herein. Overall, the ZAP has been shown to be a sensitive and generic method with a diverse range of applications. This technique can be used to predict product quality and purification yields. A classification system (see Table 5) for assigning a quality rating was designed to categorize the quality of a fermenter and its harvest for monitoring purposes. The classification system used for rFVIII should be useful for other proteins of interest, too. See Table 6. Furthermore, the correlation can also be used to determine the potential of the harvest for purification processing without having to actually carry out the purification.

The above examples described where this technique has been applied to elucidate the potential for purification of rFVIII and the correlation between the quality of rFVIII as determined by ZAP and the yield from a chromatography process. The above examples are intended to illustrate the invention and it is thought variations will occur to those skilled in the art. Accordingly, it is intended that the scope of the invention should be limited only by the claims below.

REFERENCES

Alwine, J. C., Kemp, D. J. and Stark, G. R. (1977) *Proc. Natl. Acad Sci., USA* 74: 5350.

Deutscher, Methods in Enzymolcgy Vol. 182: Guide to Protein Purification, Academic Press, Inc. N.Y. (1990)).

Dunbar, B. S., editor in "Protein Blotting-A practical approach." Oxford University Press, 1994.

Gershoni, J. M. (1988) *Meth. Bicchem. Anal.*, 33: 1.

Kennel, S. I., Lankford P. K., Foote, L. J., Davis, I. A. (1998) *Hybridoma* 17: 509.

Kaufmnan, R., Wasley L C. and Dorner A. J. (1988) *J. Biol. Chem.* 263: 6352.

Sato, C., Inoue, S., Matsuda, T. and Kitajima, K. (1998) *Anal. Biochem.* 261: 191.

R. Scopes, Protein Purification (2d ed.), Springer-Verlag, N.Y. (1987)

Southern, E. M. (1975) *J. Mol. Biol.* 98: 503.

Towbin, H., Staehelin, T. and Gordin, J. (1979). *Proc. Natl. Acad. Sci., USA* 76: 4350.

What is claimed is:

1. A method of predicting the yield of a protein product of a purification process, wherein the protein product is obtained from cells in a fermentation medium in a fermenter system, the method comprising the steps of
   a) obtaining multiple batches of fermentation medium containing the product,
   b) subjecting individual batches from step a) to the purification process,
   c) measuring the percentage yield of the protein product of the purification process for each individual batch of step b),
   d) determining a quality rating from each individual batch of step a), wherein the quality rating is a numerical value assigned to an estimate of the percentage of desired protein product represented in the total number of barnds observed on a Western blot,
   e) determining the correlation between the yields measured in step c) and the quality ratings determined in step d),
   f) obtaining a test sample of fermentation medium from the fermenter system,
   g) determining the quality rating from the test sample, and
   h) using the correlation of step e) and the quality rating in step g) to predict the yield of the protein product of the purification process.

2. The method of claim 1, wherein the Western blot assay includes a chemiluminescent detection system.

3. The method of claim 1, wherein the product is recombinant factor VIII.

4. The method of claim 3, wherein the purification process comprises the steps of
   a) contacting the factor VIII with an anion exchanger under conditions which allow the recovery of a fraction containing ion-exchange-purified factor VIII, and
   b) contacting the factor VIII with an immunoaffinity adsorbent under conditions which allow the recovery of a fraction containing affinity-purified factor VIII.

5. The method of claim 1, wherein the product is IL-2.

* * * * *

UNITED STATES PATENT AND TRADEMARK OFFICE
CERTIFICATE OF CORRECTION

PATENT NO. : 6,214,975 B1
DATED : April 10, 2001
INVENTOR(S) : Zachariou et al.

It is certified that error appears in the above-identified patent and that said Letters Patent is hereby corrected as shown below:

Column 20,
Line 8, "barnds" should read -- bands --.

Signed and Sealed this

Fifth Day of March, 2002

Attest:

Attesting Officer

JAMES E. ROGAN
Director of the United States Patent and Trademark Office